United States Patent [19]
Wang et al.

[11] Patent Number: 5,942,625
[45] Date of Patent: Aug. 24, 1999

[54] PREPARATION OF CHLOROMETHYLPYRIDINE HYDROCHLORIDES

[75] Inventors: Yuan Wang; Lu Wei Liu, both of Kirkland; Alexandre L'Heureux, St-Thomas D'aquin; Olivier Lepage, St-Hyacinthe; Diane Phelan, Montréal, all of Canada

[73] Assignee: Delmar Chemicals, Quebec, Canada

[21] Appl. No.: 09/187,402

[22] Filed: Nov. 6, 1998

[51] Int. Cl.$^6$ .................................................. C07D 213/26
[52] U.S. Cl. ................................................................ 546/346
[58] Field of Search .............................................. 546/346

[56] References Cited

U.S. PATENT DOCUMENTS 5,686,619 11/1997 Bay et al. ............................... 546/339

*Primary Examiner*—Patricia L. Morris
*Attorney, Agent, or Firm*—Sixbey, Friedman, Leedom & Ferguson, P.C.; Jeffrey L. Costellia

[57] ABSTRACT

Chloromethylpyridine hydrochlorides such as 3-chloromethylpyridine hydrochloride, an important pharmaceutical intermediate, are prepared in high yield and high purity by reacting the corresponding pyridyl carbinol with a slight excess of thionyl chloride, in solution in an inert solvent such as toluene. The pyridyl carbinol solution is added to the thionyl chloride gradually and under its surface, to prevent the formation of impurities. The product is recovered by applying vacuum or nitrogen purge to the reaction mixture to assist precipitation, followed by filtration and washing.

8 Claims, No Drawings

PREPARATION OF CHLOROMETHYLPYRIDINE HYDROCHLORIDES

FIELD OF THE INVENTION

This invention relates to chemical synthetic processes for preparing pyridine compounds, useful as synthetic intermediates in manufacture of pharmaceuticals. More specifically, it relates to processes for preparing chloromethylpyridine hydrochlorides, such as 3-chloromethylpyridine hydrochloride, otherwise known as 3-picolyl chloride hydrochloride.

BACKGROUND OF THE INVENTION AND PRIOR ART

3-Chloromethylpyridine hydrochloride, of chemical formula:

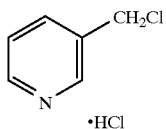

is used in the preparation of various pharmaceuticals. There is accordingly a requirement that it be produced in a highly pure form.

U.S. Pat. No. 5,686,619 Bay et al. and its parent patent U.S. Pat. No. 5,521,316 describe a process for preparing chloroalkyl pyridinium hydrochloride compounds with high purity levels and in a free-flowing, non-dusting form. In the process described in those patents, an initial, preliminary step of preparation of hydroxy alkyl pyridinium hydrochloride compound is required, involving reaction of hydroxy alkyl pyridine compound with hydrogen chloride. Then a solution or dispersion of the corresponding hydroxy alkyl pyridinium hydrochloride compound so prepared, in a medium comprising a non-solvent for the chloroalkyl pyridinium hydrochloride, is reacted with a large excess of thionyl chloride to form the chloroalkyl pyridinium hydrochloride as a solid in the reaction mixture.

It is an object of the present invention to provide a new and improved process for preparing chloromethylpyridine hydrochlorides.

SUMMARY OF THE INVENTION

The present invention provides a process for preparing chloromethylpyridine hydrochlorides which comprises reacting the corresponding pyridyl carbinol with a slight excess of thionyl chloride, in a reaction medium comprising an inert organic solvent. In the process of the present invention, accordingly, the requirement of the preliminary formation of the hydroxy alkyl pyridine hydrochloride is eliminated, thereby significantly simplifying the process and improving the economics of it. There is no evolution of HCl gas during the reaction with thionyl chloride, as happens in prior art processes, so that scrubbing and other exhaust treatment requirements are substantially reduced in the present process. Moreover, the amount of thionyl chloride reagent necessary is significantly reduced as compared with prior art processes. Thionyl chloride is a hazardous substance, the reduction in use of which is beneficial for environmental and cost reasons. The chloromethylpyridine hydrochloride is initially formed in the process of the invention as an oily semi-solid, which is readily converted to a crystalline solid in a high degree of purity, e.g. by application of a vacuum or nitrogen purge aid to complete the precipitation of the product, followed by filtration to obtain the substantially pure crystalline solid product.

DESCRIPTION OF THE PREFERRED EMBODIMENTS

An example of a suitable, preferred organic solvent for use in the process of the invention is toluene, although other similar solvents (benzene, xylenes, cyclohexane etc.) can also be used. Toluene is especially preferred on account of its low cost and low toxicity. Moreover, its use as the sole solvent in the process allows its substantial recovery for further use.

The reaction scheme can be represented as follows:

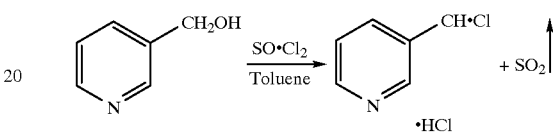

It is preferred in conducting the process of the present invention to use a scrubber containing an aqueous solution of alkali, such as sodium hydroxide, attached to the reaction vessel. Gaseous by-products of the reaction, notably sulfur dioxide flow into the scrubber as they are evolved, or purged from the reaction mixture, and are neutralized with the formation of salts such as sodium bisulfite.

The order of addition of the reagents when forming the reaction mixture preferably involves the addition of the pyridyl carbinol solution to the thionyl chloride solution, rather than the reverse. This allows for better temperature control of this exothermic reaction (the rate of addition is preferably controlled so that the reaction mixture does not exceed 35° C.), as well as permitting the operator to arrange for substantially instant mixing of the reagents, e.g. by use of a dip tube to introduce the pyridyl carbinol solution below the surface of the thionyl chloride solution, to enable the process to produce highly pure chloromethyl pyridine hydrochloride.

The slight molar excess of thionyl chloride, over that calculated for exact stoichiometry with the pyridyl carbinol, is preferably about 0.1–0.2 equivalent of excess. This contrasts with the large (1 equivalent) excesses proposed in prior art processes.

As noted, the product of the process of the invention forms initially as an oily semi-solid. The preferred recovery processes for the product are the application of vacuum, or a nitrogen purge, to the reaction suspension medium, more effectively to remove most the residual sulfur dioxide and cause the complete precipitation and crystallization of the product. Then the solid product can be readily filtered off and washed, to yield a highly pure white or off-white crystalline solid, normally in greater than 90% yield.

Whilst the process is described herein with specific reference to the production of 3-chloromethylpyridine hydrochloride, the commercially most important member of this family of compounds, it is also applicable to preparation of the regio isomers 2-chloromethylpyridine hydrochloride and 4-chloromethylpyridine hydrochloride, simply by choice of the appropriate starting material.

A specific preferred embodiment of the invention is described in detail, for illustrative purposes, in the following example.

SPECIFIC DESCRIPTION OF THE MOST PREFERRED EMBODIMENT

A dry 500 ml 3 necked round bottom flask fitted with a mechanical stirrer, thermometer and an addition funnel with nitrogen inlet was linked to a caustic scrubber. A solution of 43.66 g (0.4 mol) 3-pyridyl carbinol, in 160 ml of toluene, was prepared and placed in the addition funnel. To the flask was charged 50.96 g (0.428 mol) thionyl chloride and 40 ml toluene.

The solution in the flask was stirred and the temperature adjusted to about 25° C. Slow addition of the 3-pyridyl carbinol solution from the addition funnel was started, maintaining the reaction temperature in the range 23–35° C. A water bath was used to help maintain the reaction temperature. The reaction mixture was agitated as the addition was made under the surface of the solution, thus achieving an instant mix of the added portion.

After the addition had been completed, the reaction mixture was stirred at room temperature for 1 hour. Vacuum was applied to the reaction mixture, and agitation was continued for a period of 2 hours, during which complete precipitation of the product occurred.

The resulting suspension was filtered, and the solid product was washed with three separate 50 ml portions of toluene. It was then dried overnight under vacuum at room temperature. A yield of 63.68 g (97.0%) of 3-chloromethylpyridine hydrochloride was obtained, as a slightly off-white crystalline solid. The product had an assay of 99.1% by weight, with a 99.8% area percent purity by HPLC.

What is claimed is:

1. A process of preparing a chloromethylpyridine hydrochloride which comprises reacting the appropriate pyridyl carbinol with a small excess of thionyl chloride in a reaction medium comprising an inert organic solvent, and recovering the chloromethylpyridine hydrochloride so formed from the reaction medium.

2. The process of claim 1 wherein the excess of thionyl chloride is from about 0.1–0.2 equivalents.

3. The process of claim 2, wherein the organic solvent is toluene.

4. The process of claim 3 wherein the reaction temperature is controlled to a level of not greater than 35° C.

5. The process of claim 4 wherein the pyridyl carbinol as a solution in toluene is slowly added to a solution of thionyl chloride in toluene under constant agitation, to prevent the formation of impurities.

6. The process of claim 5 wherein the pyridyl carbinol is 3-pyridyl carbinol so as to prepare 3-chlormethylpyridine hydrochloride.

7. The process of claim 6 wherein the 3-chloromethylpyridine hydrochloride is recovered from the reaction mixture by precipitation assisted by application of vacuum applied thereto, followed by filtration.

8. The process of claim 6 wherein the 3-chloromethylpyridine hydrochloride is recovered from the reaction mixture by precipitation assisted by nitrogen purge applied thereto, followed by filtration.

* * * * *